(12) United States Patent
Guan et al.

(10) Patent No.: US 9,149,719 B2
(45) Date of Patent: Oct. 6, 2015

(54) DEVICE AND METHOD FOR GENERATING A REPRESENTATION OF A SUBJECT'S ATTENTION LEVEL

(75) Inventors: Cuntai Guan, Singapore (SG); Brahim Hamadi Charef, Singapore (SG); Haihong Zhang, Singapore (SG); Chuanchu Wang, Singapore (SG); Keng Peng Tee, Singapore (SG); Kai Keng Ang, Singapore (SG); Zheng Yang Chin, Singapore (SG); Ranga Krishnan, Singapore (SG); Tih Shih Lee, Singapore (SG); Choon Guan Lim, Singapore (SG); Daniel Fung, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 864 days.

(21) Appl. No.: 13/140,599

(22) PCT Filed: Sep. 14, 2009

(86) PCT No.: PCT/SG2009/000337
§ 371 (c)(1),
(2), (4) Date: Jan. 5, 2012

(87) PCT Pub. No.: WO2010/071604
PCT Pub. Date: Jun. 24, 2010

(65) Prior Publication Data
US 2012/0108997 A1  May 3, 2012

Related U.S. Application Data

(60) Provisional application No. 61/139,291, filed on Dec. 19, 2008.

(51) Int. Cl.
*A61B 5/04* (2006.01)
*A63F 13/40* (2014.01)
(Continued)

(52) U.S. Cl.
CPC ............... *A63F 13/10* (2013.01); *A61B 5/048* (2013.01); *A61B 5/04014* (2013.01);
(Continued)

(58) Field of Classification Search
USPC .................................................. 600/544, 545
See application file for complete search history.

(56) References Cited

U.S. PATENT DOCUMENTS

| 5,377,100 A | 12/1994 | Pope et al. |
| 5,724,987 A | 3/1998 | Gevins et al. |

(Continued)

FOREIGN PATENT DOCUMENTS

WO   2009134205 A1   11/2009

OTHER PUBLICATIONS

Cormier, E. "Attention Deficit/Hyperactivity Disorder: A Review and Update", Journal of Pediatric Nursing, vol. 23, Issue 5, Oct. 2008, pp. 345-357 (13 pgs.).

(Continued)

*Primary Examiner* — Etsub Berhanu
(74) *Attorney, Agent, or Firm* — Conley Rose, P.C.

(57) ABSTRACT

A device and method for generating a representation of a subject's attention level. The device measures brain signals from the subject; extracts temporal features from the brain signals; classifies the extracted temporal features using a classifier to give a score $X_1$; extracts spectral-spatial features from the brain signals; selects spectral-spatial features containing discriminative information between concentration and non-concentration states from the set of extracted spectral-spatial features; classifies the selected spectral-spatial features using a classifier to give a score $X_2$; combines the scores $X_1$ and $X_2$ to give a single score; and presents the score to the subject.

31 Claims, 7 Drawing Sheets

(51) Int. Cl.
 A61B 5/048 (2006.01)
 A61B 5/0482 (2006.01)
 A61B 5/00 (2006.01)
 G06F 3/01 (2006.01)
 A61B 5/0484 (2006.01)

(52) U.S. Cl.
 CPC .......... *A61B 5/04017* (2013.01); *A61B 5/0482* (2013.01); *A61B 5/7267* (2013.01); *G06F 3/015* (2013.01); *A61B 5/04842* (2013.01); *A61B 5/04845* (2013.01); *A63F 2300/1012* (2013.01); *A63F 2300/6027* (2013.01); *A63F 2300/61* (2013.01)

(56) References Cited

U.S. PATENT DOCUMENTS

| | | | |
|---|---|---|---|
| 6,402,520 | B1 * | 6/2002 | Freer ............................ 434/236 |
| 8,442,626 | B2 * | 5/2013 | Zavoronkovs et al. ........ 600/544 |
| 2002/0128540 | A1 | 9/2002 | Kim et al. |
| 2004/0152995 | A1 * | 8/2004 | Cox et al. ...................... 600/544 |
| 2005/0228515 | A1 * | 10/2005 | Musallam et al. .............. 700/83 |
| 2008/0208072 | A1 * | 8/2008 | Fadem et al. .................. 600/544 |
| 2008/0220400 | A1 * | 9/2008 | Cox et al. ...................... 434/236 |
| 2009/0156954 | A1 * | 6/2009 | Cox et al. ...................... 600/544 |
| 2009/0216146 | A1 * | 8/2009 | Teicher et al. ................. 600/544 |
| 2009/0234243 | A1 * | 9/2009 | Schneider et al. ............. 600/544 |
| 2009/0306531 | A1 * | 12/2009 | Leuthardt et al. ............. 600/544 |
| 2010/0217145 | A1 * | 8/2010 | Buscema ....................... 600/544 |
| 2010/0249636 | A1 * | 9/2010 | Pradeep et al. ................ 600/544 |
| 2010/0280403 | A1 * | 11/2010 | Erdogmus et al. ............. 600/545 |
| 2011/0313308 | A1 * | 12/2011 | Zavoronkovs et al. ........ 600/544 |
| 2012/0172743 | A1 * | 7/2012 | Aguilar et al. ................. 600/544 |

OTHER PUBLICATIONS

Snyder, et al., "Blinded, multi-center validation of EEG and rating scales in identifying ADHD within a clinical sample", Psychiatry Research, vol. 159, Issue 3, Jun. 30, 2008, pp. 346-358 (13 pgs.).
Graham, et al., "ADHD", Medicine, vol. 35, Issue 3, Mar. 2007, pp. 181-185 (5 pgs.).
Zachor, et al., "Effects of long-term psychostimulant medication on growth of children with ADHD", Research in Developmental Disabilities, vol. 27, Issue 2, Mar.-Apr. 2006, pp. 162-174 (13 pgs.).
Hamadicharef, et al., "Learning EEG-based Spectral-Spatial Patterns for Attention Level Measurement", Submitted to the 2009 IEEE International Symposium on Circuits and Systems (ISCAS2009), Taipei, Tawain, May 14-17, 2009 (4 pgs.).
Chin, et al., "Multiclass Voluntary Facial Expression Classification based on Filter Bank Common Spatial Pattern", Proceedings of the 30th Annual International Conference of the IEEE Engineering in Medicine and Biology Society (EMBC), Vancouver, Canada, Aug. 20-24, 2008 (4 pgs.).
Jones, et al., "Asymmetrical visual-spatial attention in college students diagnosed with ADD/ADHD", Cognitive and Behavioral Neurology, vol. 21, No. 3, Sep. 2008, pp. 176-178 (3 pgs.).
Engelhardt, et al., "Cognitive inhibition and working memory in attention-deficit/hyperactivity disorder", Journal of Abnormal Psychology, vol. 117, No. 3, Aug. 2007, pp. 591-605 (15 pgs.).
Brocki, et al., "Working memory in school-aged children with attention-deficit/hyperactivity disorder combined type: Are deficits modality specific and are they independent of impaired inhibitory control?", Journal of Clinical and Experimental Neuropsychology, Feb. 4, 2008, vol. 30, No. 7, pp. 749-759 (12 pgs.).
Kim, et al., "The Child Behavior Checklist Together With the ADHD Rating Scale Can Diagnose ADHD in Korean Community-Based Samples", Canadian Journal of Psychiatry, vol. 50, No. 12, Oct. 2005 (4 pgs.).
Schwean, et al., "Assessment of Attention Deficit Hyperactivity Disorder with the WISC-IV, WISC-IV Clinical Use and Interpretation", 2005, pp. 235-280 (46 pgs.).
Lubar, J. "Discourse on the development of EEG diagnostics and biofeedback for attention-deficit/hyperactivity disorders", Biofeedback and Self-Regulation, 1991, vol. 16, pp. 202-225 (25 pgs.).
Achenbach, T. "Manual for Teacher's Report Form and 1991 Profile", Burlington, VT: University of VT, Department of Psychiatry, 1991 (20 pgs.).
Ivanova, et al., "Testing the Teacher's Report Form Syndromes in 20 Societies", School Psychology Review, vol. 36, No. 3, 2007, pp. 468-483 (16 pgs.).
Rudan, et al., "The Child Behavior Checklist, Teacher Report Form and Youth Self Report Problem Scales in a Normative Sample of Croatian Children and Adolescents Aged 7-18", Coll. Antropol, vol. 29, No. 1, 2005, pp. 17-26 (10 pgs.).
Dupaul, et al., "Attention Deficit-Hyperactivity Disorder in Adolescence: Critical Assessment Parameters", Clinical Psychology Review, University of Massachusetts Medical Center, vol. 11, 1991, pp. 231-245 (15 pgs.).
Naglieri, et al., "Relationships Between the WISC-III and the Cognitive Assessment System with Conners' rating scales and continuous performance tests", Archives of Clinical Neuropsychology vol. 20, Issue 3, May 2005, pp. 385-401 (17 pgs.).
Grave, et al., "Is cognitive behavior therapy developmentally appropriate for young children? A critical review of the evidence", Clinical Psychology Review, vol. 24, Issue 4, Aug. 2004, pp. 399-420 (22 pgs.).
Elliot, et al., "A national survey of assessment and therapy techniques used by behavior therapists", Cognitive and Behavioral Practice, vol. 3, Issue 1, Summer 1996, pp. 107-125 (19 pgs.).
Whalen, C. K. "Attention-deficit/Hyperactivity Disorder (ADHD)", International Encyclopedia oft he Social & Behavioral Sciences, 2004, pp. 871-875 (5 pgs.).
Egner, et al., "The effects of neurofeedback training on the spectral topography of the electroencephalogram", Clinical Neurophysiology, vol. 115, Issue 11, Nov. 2004, pp. 2452-2460 (9 pgs.).
Besserve, et al., "Classification Methods for Ongoing EEG and MEG Signals" Biological Research vol. 40 No. 4 Santiago 2007, pp. 415-437, ISSN 0176-9760 (23 pgs.).
Fuchs, et al., Neurofeedback Treatment for Attention-Deficit/Hyperactivity Disprder in Children: A Comparison with Methylphenidate Applied Psychophysiology and Biofeedback, vol. 28, No. 1, Mar. 2003 (pp. 1-12, ISSN 1573-3270 (12 pgs.).
Hamadicharef et al; Learning EEG-Based Spectral-Spatial Patterns for Attention Level Measurement; Institute for Infocomm Research, 1 Fusionopolis Way, #21-01 Connexis, Singapore 138632; 4 pages; IEEE 2009.
Kai Keng Ang, et al.; Filter Bank Common Spatial Pattern (FBCSP) in Brain-Computer Interface; IEEE 2008; 8 pages, 2390-2397; 2008 International Joint Conference on Neural Networks (IJCNN 2008).
Wei, et al.; The Temporal and Spatial Features of Event-Related EEG Spectral Changes in 4 Mental Conditions; Institute of Space Medico-Engineering Beijing 100094, China; Accepted for Publication Nov. 24, 1997; 8 pages.

* cited by examiner

DEVICE AND METHOD FOR GENERATING A REPRESENTATION OF A SUBJECT'S ATTENTION LEVEL

FIELD OF INVENTION

The present invention relates broadly to a device and method for generating a representation of a subject's attention level, and to a computer storage medium having stored thereon computer code means for instructing a computing device to execute a method of generating a representation of a subject's attention level.

BACKGROUND

Attention Deficit Hyperactivity Disorder (ADHD) is a common behavioural disorder in children, characterised by symptoms such as inattention and hyperactivity. Today's management of ADHD often leads to the use of pharmacological stimulant medication. Parents, however, may be concerned about potential unknown side effects of these medications which include headache, stomach pain, sleeplessness, poor appetite, physical growth retardation, etc.

Recently, there has been a growing interest in treatment of ADHD based on psychosocial aspects. Although important, such treatment has, to date, been shown to be less superior compared to pharmacological treatments.

At the same time, it has been noted that advanced technologies such as brain-computer interface (BCI) can be used to improve the treatment of ADHD based on psychological aspects. BCI provides a direct communication pathway between a human brain and an external device. It relies on bio-signals such as electroencephalogram (EEG) and thus is a low cost and non-invasive interface. Various studies have demonstrated the efficacy of neurofeedback (NFB) or EEG biofeedback in the treatment of ADHD.

U.S. Pat. No. 6,402,520 describes regulating theta and beta wave activity (more specifically, to decrease theta wave activity and increase beta wave activity) as measured based on respective average millivolt activity. However, a clear and direct correlation between the measured average millivolt theta and beta activities and attention has not been established. Thus, the users involved in the training approaches in that document only learn to control their measured average millivolt theta and beta activities, which are not a direct measure of attention. As a result, while the users may develop a mechanism for controlling the measured average millivolt theta and beta activities, this does not directly correlate with achieving higher attention levels.

A need therefore exists to provide device and method for generating a representation of a subject's attention level that seek to address at least one of the above problems.

SUMMARY

In accordance with a first aspect of the present invention, there is provided a device for generating a representation of a subject's attention level comprising:

means for measuring brain signals from the subject;
means for extracting temporal features from the brain signals;
means for classifying the extracted temporal features using a classifier to give a score $x_1$;
means for extracting spectral-spatial features from the brain signals;
means for selecting spectral-spatial features containing discriminative information between concentration and non-concentration states from the set of extracted spectral-spatial features;
means for classifying the selected spectral-spatial features using a classifier to give a score $x_2$;
means for combining the scores $x_1$ and $x_2$ to give a single score; and
means for presenting said score to the subject.

The means for presenting may present said score in the form of a game.

The means for presenting said score may adaptively adjust at least one control parameter of the game based on said score.

The adjusting of said one parameter may comprise:
presenting said game using a relationship between said score and said one control parameter over a first period of time;
determining a representative value for the score of the subject over the first period of time;
adjusting the relationship based on said representative value; and
presenting said game using the modified relationship between said score and said one control parameter over a second period of time.

The adjusting of the relationship may be such that a level of difficulty of the game in the second period of time is proportional to the representative value over the first period.

The extracting of the temporal features from the brain signals may comprise:
computing statistics of brain waveforms in each of a plurality of electrode channels; and
concatenating the statistics into a joint feature vector.

The statistics of the brain waveforms may be standard deviations.

The extracting of the spectral-spatial features of the brain signals may comprise:
extracting respective brain signal components in discrete frequency windows using filter banks to obtain spectral features of brain signals; and
applying a CSP algorithm to each of the spectral features using a CSP array to obtain the spectral-spatial features of brain signals.

The selecting of the spectral-spatial features containing discriminative information between concentration and non-concentration states from the set of extracted spectral-spatial features may comprise selecting spectral-spatial features based on the mutual dependence of the features with respect to the concentration and non-concentration states.

The combining of the scores $x_1$ and $x_2$ to give a single score may comprise:
normalizing the scores $x_1$ and $x_2$ according to an equation $(x-m_x)/s_x$, wherein $m_x$ and $s_x$ are the mean and standard deviation of outputs from the classifiers using training samples to give $x_{1n}$ and $x_{2n}$ respectively;
assigning weights $w_1$ and $w_2$ to normalized scores $x_{1n}$ and $x_{2n}$ respectively; and
combining the scores $x_{1n}$ and $x_{2n}$ according to an equation $x_{1n}*w_1+x_{2n}*w_2$ to give a single score.

The weights $w_1$ and $w_2$ may be calculated according to the equation $w_i=(y_i)^p$ where $y_i$ is a classification accuracy in classifying the extracted temporal features if i=1 and in classifying the extracted spectral-spatial features if i=2 and p (p>0) controls the power of $w_i$ in the calculation of the single score.

The classifier may comprise one or more of a group consisting of a Linear Discriminant Analysis classifier, Neural Networks, Support Vector Machines, Fuzzy Inference System, Tree-based classifiers, Fuzzy Type 2 and Relevance Vector Machine.

The device may use training data to generate parameters for classifying the extracted temporal features using a classifier, for extracting spectral-spatial features from brain signals, for selecting spectral-spatial features containing discriminative information between the concentration and non-concentration states from the set of extracted spectral-spatial features and for classifying the selected spectral-spatial features using a classifier.

The parameters may comprise one or more of a group consisting of projection matrices of common spatial patterns (CSPs) for the CSP algorithm, parameters for selecting spectral-spatial features based on mutual information and a model for the classifiers.

The use of training data to generate parameters may comprise:

collecting training data from subjects performing a set of tasks; and determining said parameters via machine learning methods.

In accordance with a second aspect of the present invention, there is provided a method for generating a representation of a subject's attention level, the method comprising the steps of:

measuring brain signals from the subject;
extracting temporal features from the brain signals;
classifying the extracted temporal features using a classifier to give a score $x_1$;
extracting spectral-spatial features from the brain signals;
selecting spectral-spatial features containing discriminative information between concentration and non-concentration states from the set of extracted spectral-spatial features;
classifying the selected spectral-spatial features using a classifier to give a score $x_2$;
combining the scores $x_1$ and $x_2$ to give a single score; and
presenting said score to the subject.

The presenting of said score to the subject may comprise presenting said score in the form of a game.

The presenting of said score to the subject may comprise adaptively adjusting at least one control parameter of the game based on said score.

The adjusting of said one parameter may comprise:
presenting said game using a relationship between said score and said one control parameter over a first period of time;
determining a representative value for the score of the subject over the first period of time;
adjusting the relationship based on said representative value; and
presenting said game using the modified relationship between said score and said one control parameter over a second period of time.

The adjusting of the relationship may be such that a level of difficulty of the game in the second period of time is proportional to the representative value over the first period.

The extracting of the temporal features from the brain signals may comprise:
computing statistics of brain waveforms in each of a plurality of electrode channels; and
concatenating the statistics into a joint feature vector.

The statistics of the brain waveforms may be standard deviations.

The extracting of the spectral-spatial features of the brain signals may comprise:
extracting respective brain signal components in discrete frequency windows using filter banks to obtain spectral features of brain signals; and
applying a CSP algorithm to each of the spectral features using a CSP array to obtain the spectral-spatial features of brain signals.

The selecting of the spectral-spatial features containing discriminative information between concentration and non-concentration states from the set of extracted spectral-spatial features may comprise selecting spectral-spatial features based on the mutual dependence of the features with respect to the concentration and non-concentration states.

The combining of the scores $x_1$ and $x_2$ to give a single score may comprise:
normalizing the scores $x_1$ and $x_2$ according to an equation $(x-m_x)/s_x$, wherein $m_x$ and $s_x$ are the mean and standard deviation) of outputs from the classifiers using training samples to give $x_{1n}$ and $x_{2n}$ respectively;
assigning weights $w_1$ and $w_2$ to normalized scores $x_{1n}$ and $x_{2n}$ respectively; and
combining the scores $x_{1n}$ and $x_{2n}$ according to an equation $x_{1n}*w_1+x_{2n}*w_2$ to give a single score.

The weights $w_1$ and $w_2$ may be calculated according to the equation $w_i=(y_i)^p$ where $y_i$ is a classification accuracy in classifying the extracted temporal features if i=1 and in classifying the extracted spectral-spatial features if i=2 and p (p>0) controls the power of $w_i$ in the calculation of the single score.

The classifier may comprise one or more of a group consisting of a Linear Discriminant Analysis classifier, Neural Networks, Support Vector Machines, Fuzzy Inference System, Tree-based classifiers, Fuzzy Type 2 and Relevance Vector Machine.

The method may further comprise using training data to generate parameters for classifying the extracted temporal features using a classifier, for extracting spectral-spatial features from brain signals, for selecting spectral-spatial features containing discriminative information between the concentration and non-concentration states from the set of extracted spectral-spatial features and for classifying the selected spectral-spatial features using a classifier.

The parameters may comprise one or more of a group consisting of projection matrices of CSPs for the CSP algorithm, parameters for selecting spectral-spatial features based on mutual information and a model for the classifiers.

The use of training data to generate parameters may comprise:
collecting training data from subjects performing a set of tasks; and
determining said parameters via machine learning methods.

In accordance with a third aspect of the present invention, there is provided a computer storage medium having stored thereon computer code means for instructing a computing device to execute a method of generating a representation of a subject's attention level, the method comprising the steps of:

measuring brain signals from the subject;
extracting temporal features from the brain signals;
classifying the extracted temporal features using a classifier to give a score $x_1$;
extracting spectral-spatial features from the brain signals;
selecting spectral-spatial features containing discriminative information between concentration and non-concentration states from the set of extracted spectral-spatial features;
classifying the selected spectral-spatial features using a classifier to give a score $x_2$;
combining the scores $x_1$ and $x_2$ to give a single score; and
presenting said score to the subject.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Example embodiments of the present invention provide a BCI-based system that seeks to improve ADHD treatment, e.g. improving attention of a user. The BCI technology of the example embodiments has been implemented in the form of computer games. Players can control, using their degree/level of attention and the BCI setup, various parameters of games, e.g. fish jump, racing car with speed, puzzle parts, etc.

Figure 1:
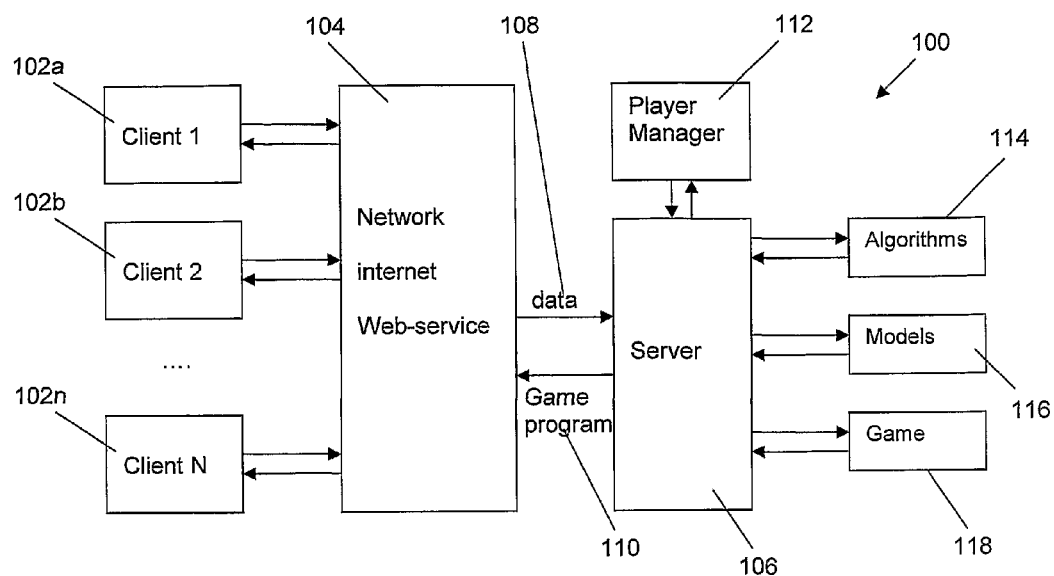
FIG. 1 shows a schematic diagram illustrating an overview of device for generating a representation of a subject's attention level according to an example embodiment.

FIG. 1 shows a schematic diagram illustrating an overview of device 100 for generating a representation of a subject's attention level according to an example embodiment. The device 100 comprises a plurality of clients 102a, 102b . . . 102n connected to a server 106 via a network connection 104, e.g. an intranet or the Internet. The server 106 is also connected to a player manager 112 which preferably manages the interconnection and data flow for each client 102.

In the example embodiment, the client 102 initiates the start of a session, e.g. by requesting the server 106 to provide a game. The client 102 then downloads the game from the server 106. A game program 110 provided by the server 106 to the client 102 comprises, inter alia, algorithm 114 used for the EEG processing, analysis and classification, attention model 116 and the game 118 embedded therewithin. Various types of game can be developed for use in the example embodiment. While playing the game the client 102 can save and send information (i.e. data 108) back to the server 106 to update the respective player's profile stored on the player manager 112. In addition, the device 100 of the example embodiment is advantageously capable of multi-user operation. Furthermore, while playing the game, the user (i.e. player) can be shown his/her level of attention, e.g. as visual feedback. This can advantageously help the user perform better.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically, stated otherwise, and as apparent from the following, it will be appreciated that throughout the present specification, discussions utilizing terms such as "scanning", "calculating", "determining", "replacing", "generating", "initializing", "outputting", "concatenating", "extracting", "classifying", "adjusting" or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Figure 2:
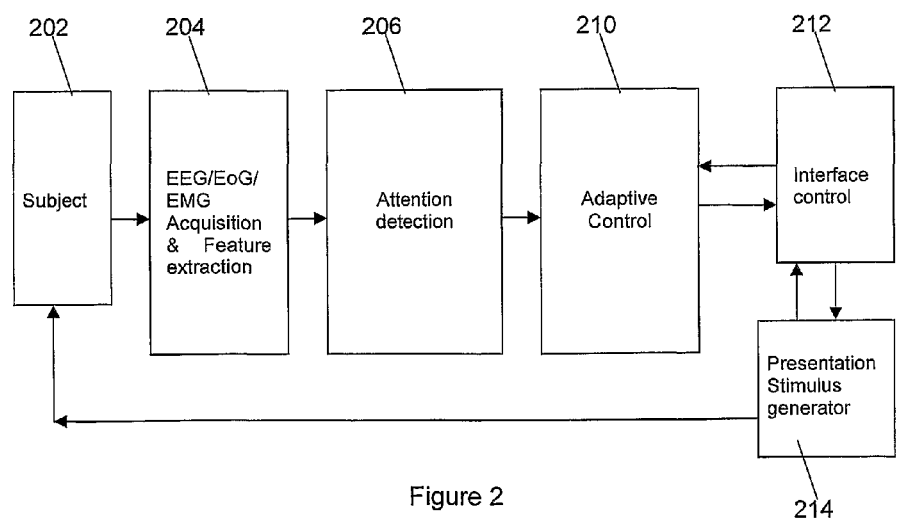
FIG. 2 is a detailed schematic diagram of an implementation of the device of FIG. 1 to one client according to an example embodiment.

FIG. 2 is a detailed schematic diagram of an implementation of the device of FIG. 1 to one client according to an example embodiment. The system comprises a physiological data acquisition module 204, an attention detection module 206, an adaptive control module 210, an interface control module 212, and a presentation module 214 with stimulus generator (for providing feedback to a subject (i.e. player) 202).

In the example embodiment, the physiological data acquisition module 204 obtains bio-signals from the subject 202 and provides the results to the attention detection module 206. The attention detection results are in turn provided to the adaptive control module 210. The interface control module 210 provides a link between the adaptive control module 210 and the presentation module 214.

Physiological Data Acquisition

In the example embodiment, the physiological data acquisition module 204 is used to record physiological bio-signals from the subject 202. The bio-signals include the electroencephalogram (EEG), electrooculogram (EoG), electromyogram (EMG). Different sensor montages can be used for data acquisition in the example embodiment. For example, for stimulation-dependent applications (e.g. P300 based games), EEG signals are collected from a central-parietal region of the scalp. For voluntary attention control, EEG signals are collected from a pre-frontal area.

In the example embodiment, the EEG signals are first passed through a filter bank to be broken down to sub-bands, where the number of bands N is variable depending on the tasks.

Let X(t) be the multi-channel EEG/EMG/EOG signal, it is filtered to generate N sub-band signals:

$$X_i(t)=f(X(t),A_i,B_i), i=1,\ldots,N \quad (1)$$

where $A_i$, $B_i$ are the coefficients of bandpass filters.

The filters in the example embodiment can be Infinite Impulse Response (IIR) or Finite Impulse Response (FIR) filters. In addition, by excluding the lower frequency filter (0-4 Hz) in the example embodiment, artifacts are advantageously removed and detection accuracy improved in the later stage.

The filtered signals are then sent to spatial filters corresponding to each frequency band. The spatial filters in the example embodiment are based on Common Spatial Pattern (CSP). The CSP filters are trained by joint maximization/minimization of the variances for two classes involved. The spatially filtered signal for $i^{th}$ band, $Y_i(t)$, is given as $$Y_i(t)=WX_i(t) \quad (2)$$

where W is the CSP projection matrix.

The rows of W are the stationary spatial filters and the columns of $W^{-1}$ are the common spatial patterns. The spatially filtered signal given in Equation (2) maximizes the differences in the variance of the two classes of EEG measurements. However, the variances of only a small number m of the spatial filtered signal are used in the example embodiment as features for classification. The m first and last rows of $Y_i(t)$ form a feature vector $O_i^t$ $$O_i^t = \log\left(\text{var}(Y_i(t)) \Big/ \sum_{i=1}^{2m} \text{var}(Y_i(t))\right) \quad (3)$$

$$\text{var}(Y_i(t)) = \sum_{\tau=t_1}^{t=t_1+t_2}(Y_i(t+\tau)-\overline{Y}_i)^T(Y_i(t+\tau)-\overline{Y}_i) \quad (4)$$

where $t_1$ and $t_2$ are the starting and ending times of a moving window respectively.

The feature vectors for classification are formed by concatenating all CSP features from sub-bands as follows $$O^t=[O_1^t, O_2^t \ldots, O_N^t] \quad (5)$$

In the method and system of the example embodiment, these feature vectors are used for attention detection. Based on specific tasks, different features are selected and finally a classification is applied.

Attention Detection

Generally, in the attention detection module 206, advanced pattern recognition methods are used in the example embodiment to process the incoming EEG signal and classify it into attention/non-attention states with a quantifiable score to indicate the level of attention of the subject 202.

In addition, the attention detection of the example embodiment is capable of dealing with two types of scenarios. In one scenario, the subject 202 is presented with stimuli and the EEG is recorded so as to monitor the anticipatory aspect of attention, to classify signals which relate to the task presented. This is named reactive/dependent attention in the example embodiment. In another scenario, the subject 202 voluntarily directs his/her attention to the auditory and/or visual stimuli, and this is named self-paced attention. Thus, the attention detection of the example embodiment preferably provides a useful means to tackle specific aspects of attention such as spatial, verbal, and object orientation.

In the example embodiment, to use attention detection in ADHD training session, a score $S_a^t$ representing the level of attention is obtained from the attention detection module 206, i.e.:

$$S_a^t=F(O^t,\Lambda_a) \quad (6)$$

where F denotes function, $O^t$ is obtainable from Equation (5) and $\Lambda_a$ denotes model parameters for attention detection, which is built upon the EEG/EMG/EOG data collected during a calibration period when the subject is asked to perform attention/relaxation tasks.

In the following, an example implementation of obtaining the score $S_a^t$ from the brain signals is described in detail and named "Hybrid EEG Model".

Figure 3:
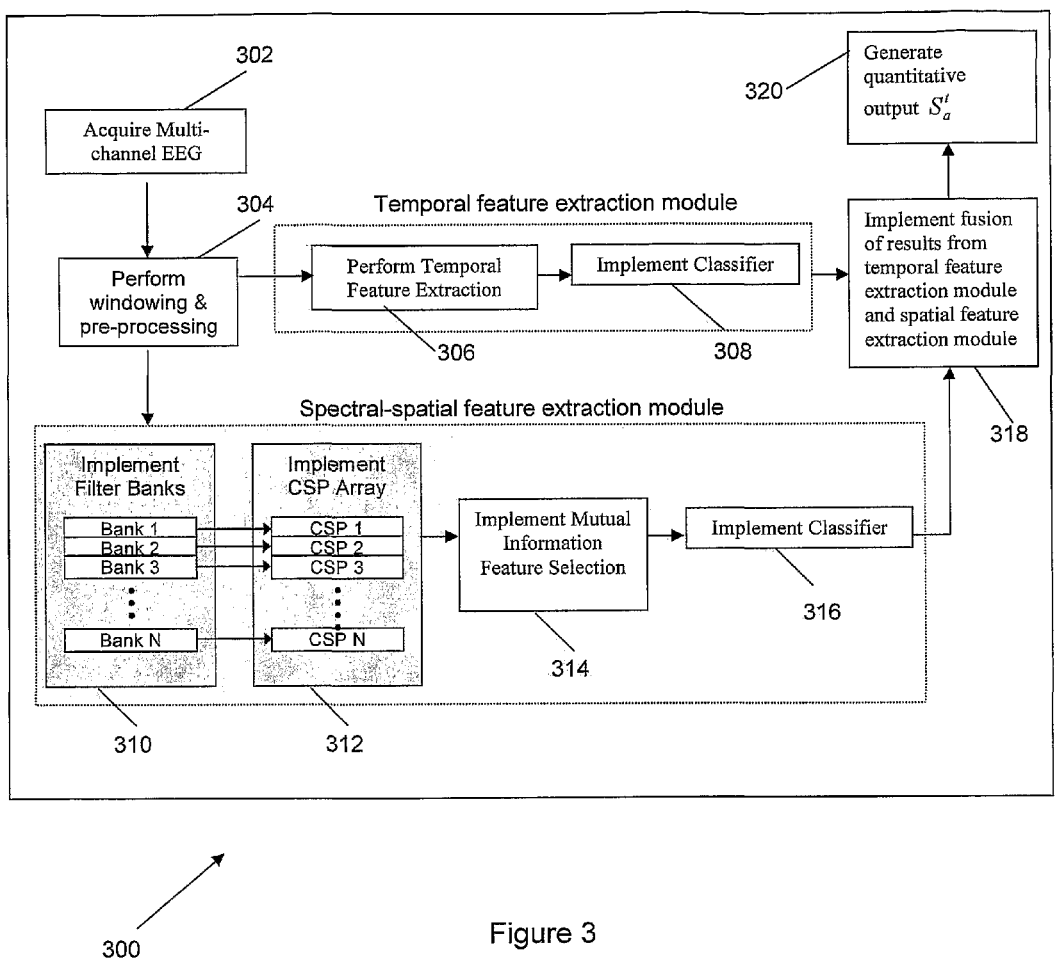
FIG. 3 shows a flowchart illustrating a method for concentration detection according to an embodiment of the present invention.

FIG. 3 shows a flowchart illustrating a method 300 for concentration detection according to an embodiment of the present invention. In step 302, multi-channel EEG acquisition is performed using a real-time data acquisition and processing platform. In one example, the data acquisition and processing platform implements the following steps. A NuAmps device from Neuroscan, Inc. is first used to measure the scalp brain signals. The brain signals are then recorded from Ag—AgCl electrodes placed on the surface of the user's head. The digitizer device for the recording of the brain signals works at a sampling rate of 250 Hz. The recorded brain signals are then filtered via temporal filtering to remove high frequency noises and very slow waves using for example, a $5^{th}$-order digital Butterworth filter with a passband of [0.5 Hz 40 Hz]. The filtered brain signals are next downsampled by a factor of 4 in order to reduce the computational complexity.

In step 304, windowing and pre-processing are performed. Step 304 selects electrode channels of interest and segments the incoming data stream into chunks using a running windowing mechanism. The window size and shift step are determined using training data. Step 304 also removes noise and artifacts through filtering.

In step 306, temporal feature extraction is performed. Step 306 computes statistics such as the standard deviation of the windowed and pre-processed EEG waveforms in each channel. The statistics are then concatenated into a joint feature vector. The feature vector is then input to step 308. In step 308, a classifier, such as the Linear Discriminant Analysis (LDA), is implemented to produce a score, for example $x_1$, indicating the likelihood of the hypothesis whereby the hypothesis is that the subject is in a state of concentration i.e. with focused attention. Other classifiers that can be used include Neural Networks (NNs), Support Vector Machines (SVM), Fuzzy Inference System (FIS), Tree-based classifiers etc., and their variants such as the Fuzzy Type 2 and the Relevance Vector Machine (RVM). Steps 306 and 308 form the temporal feature extraction module in the method 300.

In step 310, an array of band pass filters i.e. filter banks is implemented on the windowed and pre-processed EEG. Each filter bank is centred at a particular frequency, sampled at a fixed interval and is used to extract the EEG component in each discrete frequency window. For example, the fixed interval may be 4 Hz for the frequency range of the EEG from 4 Hz to 36 Hz. In one example, the filter bank is a digital filter with a low order and a linear phase. Such a filter bank can be a Finite Impulse Response (FIR) filter or an Infinite Impulse Response (IIR) filter. In a preferred embodiment, the filter bank is a low-order bandpass Chebyshev Type II filter with a pass-band width of 4 Hz. MATLAB (MathWorks Inc.) tools can be used to design and implement the filter banks. At the output of the filter banks, an EEG component is obtained for each filter bank with each component further containing separate components from each of the selected electrode channels.

In step 312, a common spatial pattern (CSP) array is implemented. Step 312 applies the CSP algorithm to each EEG component obtained in step 310 to emphasize the difference in spatial distributions of the energy between the two classes, the concentration and the non-concentration classes corresponding to the brain states during which the subject is concentrating and not concentrating respectively. The CSP algorithm is detailed in Equation (7) whereby for the $j^{th}$ EEG component, a CSP feature cf(j) is extracted according to Equation (7). In Equation (7), $W_I$ is a matrix comprising of the first $I_1$ and the last $I_2$ rows of W, whereby $I_1$ and $I_2$ are normalized for data processing efficiency and the ratio between $I_1$ and $I_2$ is kept constant. Furthermore, $E_j$ is a m×n data matrix of the $j^{th}$ EEG component whereby m is the number of selected electrode channels and n is the number of samples in the EEG component in one channel. The relationship between W and the covariance matrices of the EEG components is given by Equation (8) in which $\Sigma^{(1)}$ and $\Sigma^{(2)}$ are the covariance matrices of the EEG components corresponding to two different classes of brain signals (i.e. different brain states), I is the identity matrix and D is a diagonal matrix.

$$cf(j) = \mathrm{diag}\left(W_I \frac{E_j E_j^T}{\mathrm{trace}(E_j E_j^T)} W_I^T\right) \quad (7)$$

$$W\Sigma^{(1)}W^T = D, \; W\Sigma^{(2)}W^T = I - D \quad (8)$$

The spatial filtering parameters i.e. spatial patterns such as the matrix W are learnt from the examples of the two classes via a subject dependent model training approach which would be elaborated later. The CSP array produces an array of spectral-spatial features, each representing the energy of the EEG component projected onto a particular spatial pattern. Such an array of features is usually over-redundant since not every spectral-spatial feature is associated with the concentration or non-concentration state in the brain. Preferably, the unnecessary (i.e. redundant) features are removed.

In step 314, a mutual information feature selection is implemented to remove the unnecessary features. Step 314 selects a set of features that contains the discriminative information between the concentration and the non-concentration states. This set is determined through a model training procedure via a subject dependent model training approach which would be elaborated later. At the end of step 314, a feature vector is obtained and is input into step 316.

In step 316, a classifier such as the LDA is implemented. Using the feature vector input from step 314, a score, for example $x_2$, is produced by the classifier. This score indicates the likelihood of the hypothesis whereby the hypothesis is that the subject is in a state of concentration i.e. with focused attention. Steps 310-316 form the spectral-spatial feature extraction module of the method 300.

Step 318 implements the fusion of the results from the temporal feature extraction module and the spectral-spatial feature extraction module to obtain a single output. In step 318, the continuous outputs of the classifiers in the temporal feature extraction module and the spectral-spatial feature extraction module are normalized. In one example, if an output is the score x, the normalized output $x_n$ will be $(x-m_x)/s_x$ whereby $m_x$ and $s_x$ are respectively the mean and standard deviation of the outputs obtained using the training samples. Two normalized outputs $x_{1n}$ and $x_{2n}$ from the temporal feature module and the spectral-spatial module respectively are hence obtained. In one example, these two normalized outputs $x_{1n}$ and $x_{2n}$ are combined according to Equation (9) using weights $w_1$ and $w_2$ whereby weights $w_1$ and $w_2$ correspond to $x_{1n}$ and $x_{2n}$ respectively and reflect the individual performance of each of the modules. However, the normalized outputs $x_{1n}$ and $x_{2n}$ can also be combined using non-linear methods such as a non-linear weighted regression. Weights $w_1$ and $w_2$ are calculated according to the formula $w_i=(y_i)^p$ where $y_i$ is the classification accuracy of the module alone and is obtained via training samples, and p (p>0) controls the power of the accuracy's weight in the combination. In one example, p is set to 1.

$$S_a^t = x_{1n} * w_1 + x_{2n} * w_2 \quad (9)$$

In step 320, a quantitative output $S_a^t$ is generated.

Because of the large cross-subject variances in EEG patterns, a subject-dependent model training approach is used in the embodiments of the present invention to obtain the parameters and models for the method 300.

Figure 4:
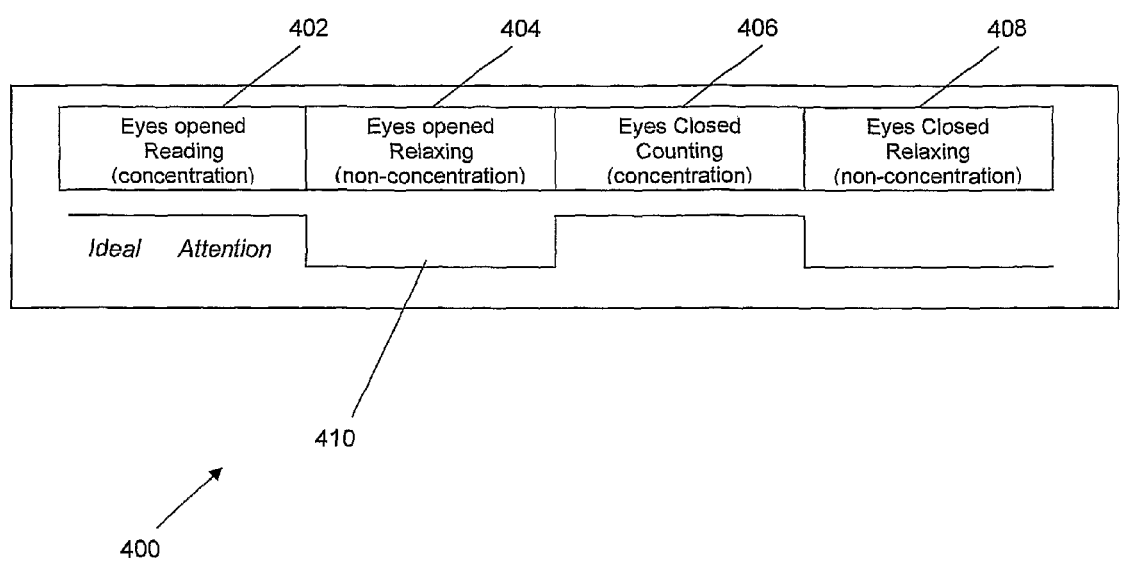
FIG. 4 illustrates a data collection protocol for a subject-dependent model training approach according to an embodiment of the present invention.

In the subject-dependent model training approach in the example embodiments, training data collection sessions are implemented to collect a subject's EEGs during navigated sessions. FIG. 4 illustrates a data collection protocol 400 for the subject-dependent model training approach according to an embodiment of the present invention. The protocol consists of 4 different tasks to be performed by the subject. In task 402, a subject is required to read a technical paper hence, in this task, the subject is in a state of concentration with his or her eyes opened. In task 404, the subject is required to relax and look around hence, in this task, the subject is not in a state of concentration and has his or her eyes opened. In task 406, the subject is required to perform mental arithmetic for example, taking 400 minus 7 repeatedly, hence, in this task, the subject is in a state of concentration with his or her eyes closed. In task 408, the subject is required to have his or her body and mind in a resting state with his or her eyes closed, hence in this task, the subject is not in a state of concentration with his or her eyes closed. The ideal level of attention for each of these tasks is plotted in FIG. 4 as line 410 whereby the ideal level of attention is high when the subject is required to be in a state of concentration and is low when the subject is required to be not in a state of concentration. In one example, the subject is required to take part in a few sessions, each session involving an array of alternate tasks.

Furthermore, in the subject-dependent training approach in the example embodiments, groups of parameters are determined via machine learning methods. An example of a machine learning method is the automation parameter optimization which is an iterative approach. Further details of the machine learning methods are given below. In one example, three groups of parameters are generated.

Firstly, projection matrices of CSPs for the CSP algorithm in the spectral-spatial feature extraction module (See FIG. 3) are obtained. The learning of these projection matrices are carried out using the CSP method that jointly diagonalizes the two covariance matrices of the two classes i.e. the concentration class and the non-concentration class.

In one example, the CSP method includes the following steps.

In step 1, the normalized spatial covariance $\Sigma$ of the EEG measurements is computed according to Equation (10). In Equation (10), E is an N×T matrix representing the raw EEG measurement data of a single trial, N is the number of channels, T is the number of measurement samples per channel, ' denotes the transpose operator and trace(•) denotes the operation that sums the diagonal elements.

$$\Sigma = \frac{EE'}{\mathrm{trace}(EE')} \quad (10)$$

In step 2, the composite spatial covariance $\Sigma_c$ is computed according to Equation (11). In Equation (11), the spatial covariance of one distribution $\bar{\Sigma}_d$ is taken to be the average over the trials of each class and d∈{1, 2} is the class index.

$$\Sigma_c = \bar{\Sigma}_1 + \bar{\Sigma}_2 \quad (11)$$

In step 3, the whitening transformation matrix P is computed according to Equation (12). In Equation (12), I is the identity matrix.

$$P\Sigma_c P' = I \quad (12)$$

In step 4, the whitened spatial covariance of the two classes is computed according to Equation (13). In Equation (13), $E_1$ and $E_2$ share common eigenvectors B as shown in Equation (14) where I is the identity matrix and is the diagonal matrix of eigenvalues.

$$\Sigma_1 = P\bar{\Sigma}_1 P' \text{ and } \Sigma_2 = P\bar{\Sigma}_2 P' \quad (13)$$

$$\Sigma_1 = B\lambda B' \text{ and } \Sigma_2 = B(I-\lambda)B' \quad (14)$$

In step 5, the CSP projection matrix W is computed according to Equation (15). In Equation (15), the rows of W are the stationary spatial filters and the columns of $W^1$ are the common spatial patterns.

$$W = B'P \quad (15)$$

The spatial filtered signal Z of a single trial EEG E is given according to Equation (16).

$$Z = WE \quad (16)$$

Equation (16) is equivalent to equation (2).

The spatial filtered signal Z given in Equation (16) maximizes the difference in the variance of the two classes of EEG measurements. In general, the variances of only a small number m of the spatial filtered signals are used as features for classification. The signals $Z_p$, p∈{1 ... 2m} that maximize the difference in the variance of the two classes of EEG are associated with the largest eigenvalues λ and (I-λ). In one example, these signals are used to form the feature vector $X_p$ given in Equation (17) whereby feature vectors $X_p$ are inputs to the classifier.

$$X_p = \log\left(\text{var}(Z_p) \Big/ \sum_{i=1}^{2m} \text{var}(Z_p)\right) \quad (17)$$

Equation (17) is equivalent to Equation (3).

Secondly, a set of parameters for mutual information feature selection in the spectral-spatial feature selection module is determined. The mutual information feature selection method is based on mutual information which indicates the mutual dependence of the features with respect to the classes. Further details of the mutual information feature selection process are as follows.

Taking into consideration a vector variable X for example, CSP features as obtained in Equation (17) and its corresponding class label Y, the mutual information between the two random variables X and Y is given by Equation (18). In Equation (18), H(X) denotes the entropy of the feature variable X and H(Y|X) represents the conditional entropy of class label variable Y given feature variable X. The entropy and the conditional entropy are given respectively in Equation (19) and Equation (20).

$$I(X; Y) = H(X) - H(Y | X) \quad (18)$$

$$H(X) = -\int_{x \in X} xp(x)\log_2 p(x)\,dx \quad (19)$$

-continued $$H(Y | X) = -\int_{x \in X} p(x) \sum_{y \in Y} P(y | x)\log_2 p(y | x)\,dx \quad (20)$$

In one example, the mutual information feature selection process includes the following steps.

In step 1, a candidate set of d features is initialized as F={$f_1$, $f_2$, ..., $f_d$} and a select feature set is initialized as a null set Fopt=ø.

In step 2, for each feature $f_k$ in the candidate set, a tentative feature vector $F_k$=Fopt∪{fk} is formed. Next, $F_k$ and the Naïve Bayesian Parzen Window are used to predict the class label $Y_k$. The mutual information of the predicted class label and the true label i.e. I($Y_k$; Y) is then computed.

In step 3, the feature $f_k$ which maximizes I($Y_k$; Y) is then selected.

In step 4, if F=ø and the gain in the mutual information is less than a preset threshold δ i.e. I($Y_k$;Y)−$I_0$<δ, the process is terminated. Otherwise, in step 5, $I_0$=I($Y_k$;Y).

In step 6, the candidate set is updated by F→F\{$f_k$} whereas the select feature set is updated by Fopt→Fopt∪S{$f_k$}.

In step 7, if the candidate set is empty, the process is terminated. Otherwise, the process is repeated from step 2.

In the example embodiments, a feature refers to a CSP feature from a filter bank and can take on different values at different instances. The mutual information feature selection process in the example embodiments as described above is applied to the training set with labelled samples. After the feature selection process is completed, the select set of features includes the CSP features determined as "important" or characteristic for concentration detection based on their mutuality amongst the labeled samples. This set of features is used during the feature selection process when processing unlabelled data for concentration detection.

Thirdly, models for the classifiers in the method 300 are obtained by the traditional Fisher linear discriminant method, using labelled training data samples. In one example, the labelled training data samples have positive labels if they are recorded from the concentration tasks and negative labels if they are recorded from the non-concentration tasks.

In the example embodiments, the set of parameters obtained from the subject dependent training approach can be used to recreate a model for concentration detection using a computer program. In one example, a setup/configuration file is created whereby this file includes the projection vector and the bias of the classifiers, projection matrices of each CSP filter, the bands to be selected for the filter banks, and the weights to be used for combining the outputs from the temporal feature extraction module and the spectral-spatial feature extraction module.

Figure 5:
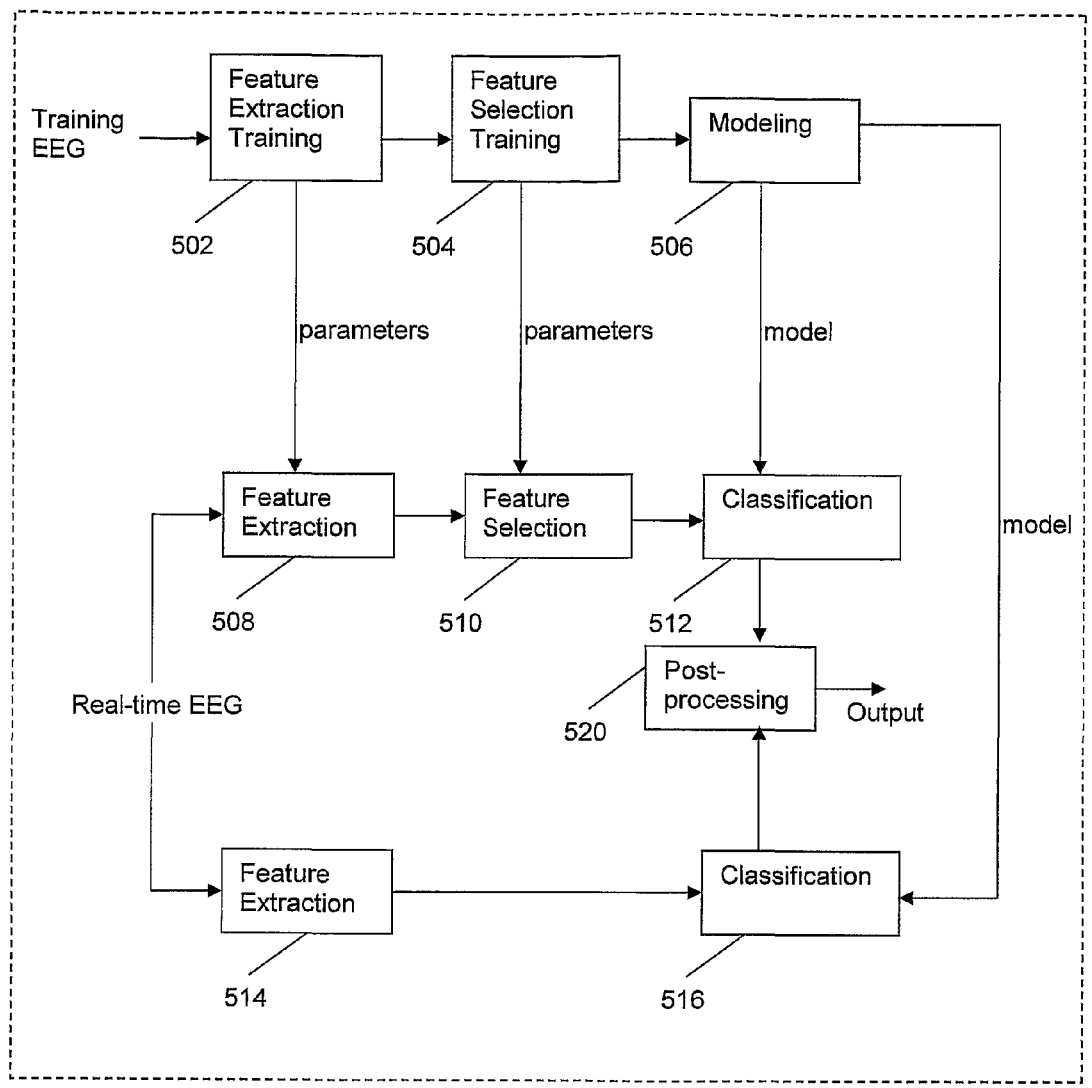
FIG. 5 shows a schematic block diagram illustrating the connection between a method for concentration detection and a subject-dependent training approach according to an embodiment of the present invention.

FIG. 5 shows a schematic block diagram illustrating the connection between a method for concentration detection and a subject-dependent training approach according to an embodiment of the present invention. In one example, units 502, 504 and 506 correspond to the subject-dependent training approach, units 508, 510 and 512 correspond to the spectral-spatial feature extraction module in the method 300 in FIG. 3 and units 514 and 516 correspond to the temporal feature extraction module in the method 300 in FIG. 3.

In FIG. 5, training EEGs are acquired from the subjects when they are performing the required tasks during the training data collection sessions implemented in the subject-dependent training approach in the example embodiments. Machine learning techniques are then implemented in using the training EEGs in the feature extraction training unit 502, feature selection training unit 504 and the modelling unit 506 in FIG. 5. This would obtain the required parameters and model for the feature extraction unit 508, feature selection unit 510 and the classification units 512 and 516 for the online processing of real-time EEGs.

In FIG. 5, in one example, the feature extraction unit 508 implements steps 310 and 312 in FIG. 3 whereas the feature extraction unit 514 implements the step 306. In addition, the feature selection unit 510 implements the step 314. Furthermore, the classification units, 516 and 512, implement steps 308 and 316 in FIG. 3 respectively whereas the post-processing unit 520 implements steps 318 and 320 in FIG. 3.

The advantages conferred by the embodiments of the present invention can include:

Firstly, the method for concentration detection in the example embodiments provides an accurate quantitative measure of the subject's attention or concentration level that is not provided by any of the prior arts. The method in the example embodiments is subject-specific and uses optimized parameters. On the other hand, the prior art methods are based on spectral features alone, with their output typically based on the average of a large set of results and a comparison performed within a narrow range to detect concentration. For example, the range can be extending from the mean minus the standard deviation to the mean plus the standard deviation of the results. Hence, the method in the example embodiments is more accurate. Furthermore, in the example embodiments of the present invention, an accurate score can be obtained continuously and this is important in (near) real-time situations when a fast and accurate score is necessary.

Secondly, the hybrid model approach implemented in the example embodiments of the present invention takes all dimensions of the EEG into consideration. Specifically, these dimensions are the temporal, spatial and spectral information of the EEG which are then combined to give a single result. On the other hand, prior arts only concentrate on the spectral information of the EEG and hence provide a less detailed picture of the subject's EEG characteristics as compared to the embodiments of the present invention. In addition, in the example embodiments, the windowing approach allows the method of concentration detection to adjust the time resolution by changing the time segmentation window size to the best window size. This allows different window sizes to be chosen under different circumstances. For example, when a long term score is desired, the EEG recording session is preferably long whereas in a real-time situation, the EEG recording segment is preferably short.

Thirdly, the method in the example embodiments of the present invention allows the creation of the best model for each subject. The method can also be used to create models based on a small cohort and thus, investigate group-specific issues for example, a group of ADHD boys. Furthermore, using a large database, the method can also be useful in investigating generalization issues for example population based medical studies.

Fourthly, in the example embodiments, automatic selection and combination of features is achieved as the parameters and models for the method are automatically obtained from subject-specific modelling. This can improve the performance of the concentration detection method in the example embodiments. The mutual information feature selection in the example embodiments provides a novel way to create subject-specific modelling for example, for individualized healthcare. Furthermore, the use of the subject-specific model in the example embodiments achieves a higher accuracy and the machine learning methods used to create the subject-specific models allow the method in the example embodiments to be more flexible.

Fifthly, in the example embodiments, the metric used in the overall performance evaluation is based on receiver operating characteristics (ROC) analysis. In the example embodiments, performance curves plotting the False Positive Rate (FPR) against the False Negative Rate are used to analyze the ROC. This metric (ROC) shows objectively the true performance of the method in the example embodiments using a simple curve. It will also allow one to determine the best model to be used for each subject and also to choose a model that will fit the sensitivity and specificity requirements along the ROC curve, while taking note of the trade-off between the sensitivity and specificity.

Furthermore, the method in the example embodiments can be implemented in the form of a software tool for example, as add-ons to EEG systems or as internet-based web services. The method can also be embedded into a PDA-like medical device. Even with only a low-cost EEG acquired at a low sampling rate and from a few EEG sensors on the forehead, the method in the example embodiments is still able to provide robust attention or concentration detection and scoring. Thus, the method in the example embodiments can be implemented in a simple and handy system with only forehead sensors.

Hence, the example embodiments of the present invention can provide a continuous, quantitative, accurate and robust scoring mechanism for subject attention or concentration level since the example embodiments are based on features extracted and further selected using a multi-domain (spatial, spectral and temporal) analysis of the EEG and classified using machine learning. In addition, the example embodiments of the present invention provide a system to capture subject-specific EEG characteristics into a computational model and an automated parameter selection process that can find the best parameters and model. Furthermore, the example embodiments of the present invention provide a post-processing fusion scheme that improves performance by a multi-scale approach.

To further illustrate the advantages of the example embodiments of the present invention, an experimental study involving 5 participating subjects (all male and healthy) was carried out. The EEGs from these subjects are recorded from a standard 10/20 EEG system (NeuroScan NuAmps) with 15 channels and from frontal channels (Fp1/Fp2).

Table 1 shows the results achieved by a method for concentration detection according to an embodiment of the present invention and by the prior art method in Monastra and Lubar [Monastra and Lubar, 2000—US06097980—Quantitative electroencephalographic (QEEG) process and apparatus for assessing attention deficit hyperactivity disorder; V. J. Monastra, S. Lynn, M. Linden, J. F. Lubar, J. Gruzelier, and T. J. LaVaque, "Electroencephalographic Biofeedback in the Treatment of Attention-Deficit/Hyperactivity Disorder," Applied Psychophysiology and Biofeedback, vol. 30, no. 2, pp. 95-114, June 2005.] In Table 1, the row, corresponding to "Theta/beta (prior-art)" shows the mean accuracy obtained by the method according to the prior art, the row corresponding to "Waveform only" shows the mean accuracy obtained from the temporal feature extraction module alone the row corresponding to "Spectrum only" shows the mean accuracy obtained from the spectral-spatial feature extraction module alone and the row corresponding to "Hybrid technique" shows the mean accuracy obtained from the method in the example embodiments. Furthermore, the results in Table 1 are in percentage, expressed in the form "mean±standard deviation" and are obtained via a 2×2 fold cross-validation method. From Table 1, it can be seen that the mean accuracy of the method in the example embodiments is significantly better than that of the prior art method. More specifically, the overall performance improvement (absolute value) of the method in the example embodiments over the prior art method is 14.8%. Thus, these results demonstrate the ability of the method in the example embodiments to create an optimized subject-specific model that outperforms the prior art method.

TABLE 1

|  | Subject 1 | Subject 2 | Subject 3 | Subject 4 | Subject 5 | Average |
| --- | --- | --- | --- | --- | --- | --- |
| Theta/beta (prior-art) | 57.5 ± 2.7 | 57.5 ± 3.5 | 66.7 ± 10.9 | 56.9 ± 9.7 | 57.5 ± 2.2 | 59.2 |
| Waveform only | 60.2 ± 3.8 | 78.8 ± 5.3 | 69.8 ± 4.7 | 76.3 ± 5.3 | 72.8 ± 6.2 | 71.6 |
| Spectrum only | 64.4 ± 4.0 | 87.9 ± 6.2 | 72.8 ± 3.2 | 76.3 ± 0.0 | 59.6 ± 8.9 | 72.2 |
| Hybrid technique | 62.8 ± 4.4 | 83.8 ± 3.5 | 76.0 ± 1.0 | 76.3 ± 1.7 | 71.3 ± 5.3 | 74.0 |
| Improvement | 5.3 | 26.3 | 9.3 | 19.4 | 13.8 | 14.8 |

Table 2 shows further results achieved by a method for concentration detection according to an embodiment of the present invention and by the prior art method in Monastra and Lubar. In Table 2, for each subject, the row corresponding to "Theta/beta (prior-art)" shows the equal error rate (EER) obtained by the method according to the prior art, the row corresponding to "Waveform only" shows the EER obtained from the temporal feature extraction module alone, the row corresponding to "Spectrum only" shows the EER obtained from the spectral-spatial feature extraction module alone and the row corresponding to "Hybrid technique" shows the EER obtained from the method in the example embodiments. The EER is the rate at which the false positive rate and the false negative rate are equal. Furthermore, the results in Table 2 are in percentage, expressed in the form "mean±standard deviation" and are obtained via a 2×2 fold cross-validation method. For each subject, the best performance by each of the methods is tabulated in Table 2. The relative error reduction rate is calculated according to Equation (21). It can be seen from Table 2 that the overall error rate reduction is 42.5% indicating that the method in the example embodiments performs significantly better than the prior art method. Furthermore, Table 2 also shows that even the performance of the temporal feature extraction module alone ("Waveform only") or the spectral-spatial feature extraction module alone ("Spectral only") in the example embodiments is better than the prior art method. This illustrates that the subject dependent training approach can significantly improve the performance of the methods.

TABLE 2

|  | Subject 1 | Subject 2 | Subject 3 | Subject 4 | Subject 5 | Average |
| --- | --- | --- | --- | --- | --- | --- |
| Theta/beta (prior-art) | 42.7 | 44.1 | 30.6 | 39.3 | 38.7 | 39.1 |
| Waveform only | 39.2 | 17.9 | 27.5 | 17.8 | 33.9 | 27.3 |
| Spectrum only | 37.9 | 8.2 | 21.9 | 25.1 | 30.6 | 24.7 |
| Hybrid technique | 35.0 | 7.3 | 21.9 | 20.8 | 27.7 | 22.5 |
| Improvement (Relative Error Reduction Rate) | 18 | 83.4 | 28.4 | 47.0 | 29.7 | 42.5 |

$$\text{Relative Error Reduction Rate} = \frac{EER_{prior\,art} - EER_{hybrid}}{EER_{prior\,art}} \quad (21)$$

It should be appreciated that, as the system of the example embodiment makes use of direct attention detection to control e.g. a game which then provides feedback cues to the subject 202, it is actually a feedforward instead of feedback system. In other words, the game only provides a visual representation of the concentration level. Other forms of representation can also be used, e.g. a simple bar indicator.

This is a major distinction between the system of the example embodiment and prior art approaches which purely rely on feedback signals and in which the connection between attention and feedback training program is implicit. In the system of the example embodiment, the control of the game is advantageously through direct attention control. That is, the subject 202 only needs to concentrate and does not need to follow any feedback cues, and the result provided (i.e. representation of concentration level) is direct. Thus, the subject 202 knows explicitly that he is controlling if he so wishes.

Adaptive Control

The adaptive control module 210 of the example embodiment receives the results of the attention detection module 206 together with the information from the presentation module 214, and adjusts automatically and adaptively the level of difficulty of the attention training games. In addition, the rules embedded in the adaptive control module 210 are programmable.

In the example embodiment, Hierarchical Temporal Control is used. First, a probabilistic model is learnt from the attention score $S_a^t$ by fitting it with a Gaussian distribution, i.e.

$$P(S_a^t) = \frac{1}{(2\pi\sigma^2)^{1/2}} \exp\left\{\frac{1}{2\sigma^2}(S_a^t - \mu)^2\right\} \quad (22)$$

The value from Equation (22) is then converted to a fixed range between 0-100 as follows:

$$Q^t = \frac{100}{1 + \exp\{-\beta P(S_a^t)\}} \quad (23)$$

where $\beta$ is a predetermined constant.

$Q^t$ is advantageously the attention score which directly associates with the performance of a game control. In the example embodiment, a threshold R is set such that the game control (e.g. speed of a car) is proportional to the value of $\Delta$ where $$\Delta(t) = \begin{cases} Q^t - R; & \text{if } (Q^t - R) > 0 \\ 0; & \text{if } (Q^t - R) < 0 \end{cases} \quad (24)$$

For example, in the case of racing car game, the speed of the car is proportional to $\Delta$. The speed of the car is set as:

$$v(t) = \alpha \Delta(t) \quad (25)$$

where $\alpha$ is a constant which can be set initially and is subsequently adjustable e.g. from a configuration file. The distance D moved by the car over a time T is as follows:

$$D = \int_0^T v(t) dt = \alpha \int_0^T \alpha(t) dt = \alpha \overline{Q} T - \alpha R T \quad (26)$$

where $\overline{Q}$ is an average value of $Q^t$ over time T.

With the quantifiable attention score and the speed control, the adaptive control module 210 of the example embodiment is able to update the threshold R based on a performance indicator obtained from a specific subject 202 when he plays the game in his first trial. In the example embodiment, the time for a subject 202 to perform a specific task (e.g. controlling a racing car around a racing course on the screen) is defined as $T_g$, and the total distance of the course is defined as D'. The adaptive control module 210 is advantageously able to adjust the difficulty level based on the following equation:

$$R' = \overline{Q} - \frac{D'}{\alpha T_g} \quad (27)$$

Thus, the system of the example embodiment adjusts the level of difficulty (to make it more difficult or easier) from a temporal perspective. It should also be appreciated that the system of the example embodiment is preferably based on an asynchronous BCI mode, i.e. the subject 202 does not need to follow any cue in order to control the game.

Based on the above, the adaptive control module 210 works by first setting a default level of difficulty. The subject 202 then plays the game at the default level of difficulty over a first period of time. During a subsequent delay time (i.e. learning phase), the relevant parameters such as $Q^t$ and T are estimated. These provide a direct indication of the subject's concentration level. The adaptive control module 210 then changes the level of difficulty based on the estimated parameters.

The delay time in the example embodiment ranges from about 1 second to 19 seconds depending on the type of game and/or presentation. The time delay can also be automatically and adaptively adjusted by the system based on statistics of the subject's respective game profile.

Subsequently, during the training session, the parameters are continuously calculated and the difficulty level is adjusted accordingly. In the example embodiment, different thresholds R may be set for respective difficulty levels. For example, the level of difficulty is increased if the player's attention level is high (e.g. time taken to complete the racing course is below a lower limit). Similarly, the level of difficulty is decreased if the player's attention level is low (e.g. time taken to complete the racing course is above an upper limit). Various other schemes for adjusting the level of difficulty can be implemented depending on e.g. whether the game is intended to be more or less challenging. The session ends after an allocated period has passed, and the relevant session information such as highest score/level, duration at the highest level, distribution of score, etc. is stored in the system.

Interface Control

The interface control module 212 of the example embodiment comprises a typical BCI setup which comprises a multi-channel EEG cap, amplifiers and application programming interface (API) code for allowing the client 102 to record and store the physiological bio-signals (EEG, EoG, EMG, etc.).

Presentation

The presentation module 214 comprises the game part, which is the implementation of the game on the client 102 (FIG. 1), and allows interaction with the subject. Various game examples have been developed for use with the system of the example embodiment. It will be appreciated that the games are run on the client while the client is being connected to the interface control module 212 to record the subject's physiological bio-signals. In the example embodiment, the interface and game parameters are fully configurable using e.g. a graphic user interface (GUI). A Stimulus generator is also provided in the presentation module 214, allowing the creation of additional auditory and visual disturbances during the training phase. Such disturbances may advantageously influence the subject's performance and thus his/her EEG/EoG/EMG.

Figure 6:
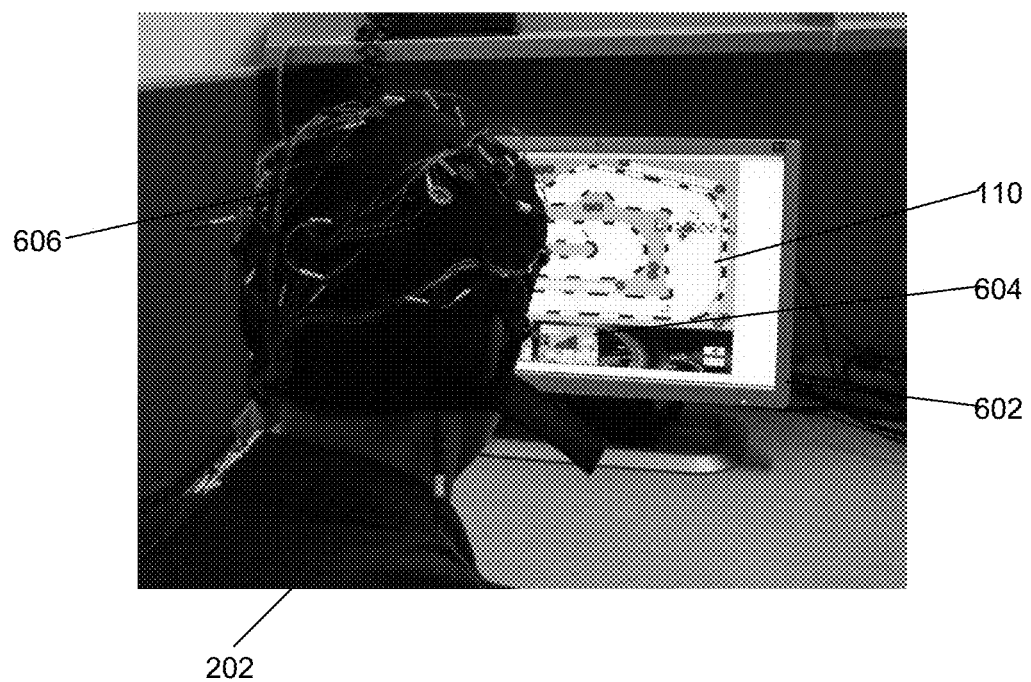
FIG. 6 shows an image of an experimental set-up for implementing the method and system of the example embodiment.

FIG. 6 shows an image of an experimental set-up for implementing the method and system of the example embodiment. As can be seen in FIG. 6, the client 102 (FIG. 1) takes the form of a standard personal computer having a display 602 in the example embodiment. The game 110 and other graphic user interface (GUI) elements 604, e.g. score, are provided on said display 602. Subject 202 plays the game 110 while wearing a cap 606 having various sensors for obtaining bio-signals generated from different areas of his/her head.

Figure 7:
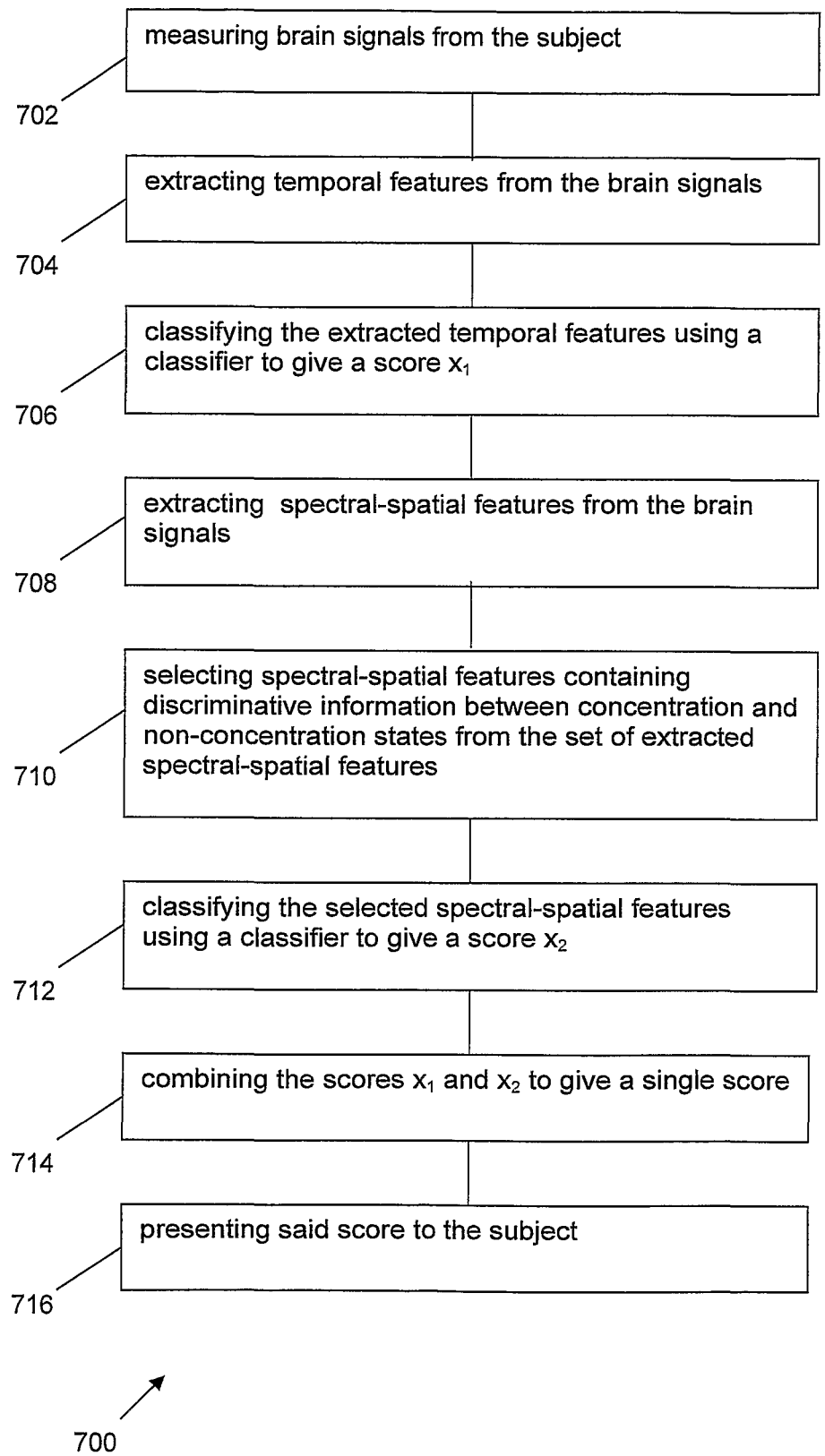
FIG. 7 shows a flow chart illustrating a method for generating a representation of a subject's attention level according to an example embodiment.

FIG. 7 shows a flow chart 700 illustrating a method 700 for generating a representation of a subject's attention level according to an example embodiment. At step 702, brain signals from the subject are measured. At step 704, temporal features are extracted from the brain signals. At step 706, the extracted temporal features are classified using a classifier to give a score $x_1$. At step 708, spectral-spatial features are from the brain signals. At step 710, spectral-spatial features containing discriminative information between concentration and non-concentration states are selected from the set of extracted spectral-spatial features. At step 712, the selected spectral-spatial features are classified using a classifier to give a score $x_2$. At step 714, the scores $x_1$ and $x_2$ are combined to give a single score. At step 716, said score is presented to the subject.

The method and system of the example embodiment described above advantageously provide an attention feedforward training protocol for attention training. In addition, the attention training game has an adjustable level of difficulty under time constraints. Further, the training system is preferably asynchronous, i.e. initiated by the user, not the computer. Advantageously, the degree/level of difficulty is adaptively and automatically adjusted by information derived from physiological bio-signals (e.g. EEG, EOG, EMG, etc.).

The method and system of the example embodiment also provide rules/strategy for programmable and automated adaptation of level of difficulty (e.g. by the Graphical User Interface (GUI) and Game). Furthermore, the parameters of the GUI/Game preferably allow the creation of a learning curve (e.g. level of difficulty over time related to training). Also, the presentation of the stimuli in a multiple sequence with additional disturbance can be created during the training. These disturbances can be auditory or/and visual, and advantageously allowing active control of the level of difficulty. The training game can also be tailored to cater for various aspects of attention (e.g. spatial, verbal, object orientation) and to provide measures of adaptive learning.

Figure 8:
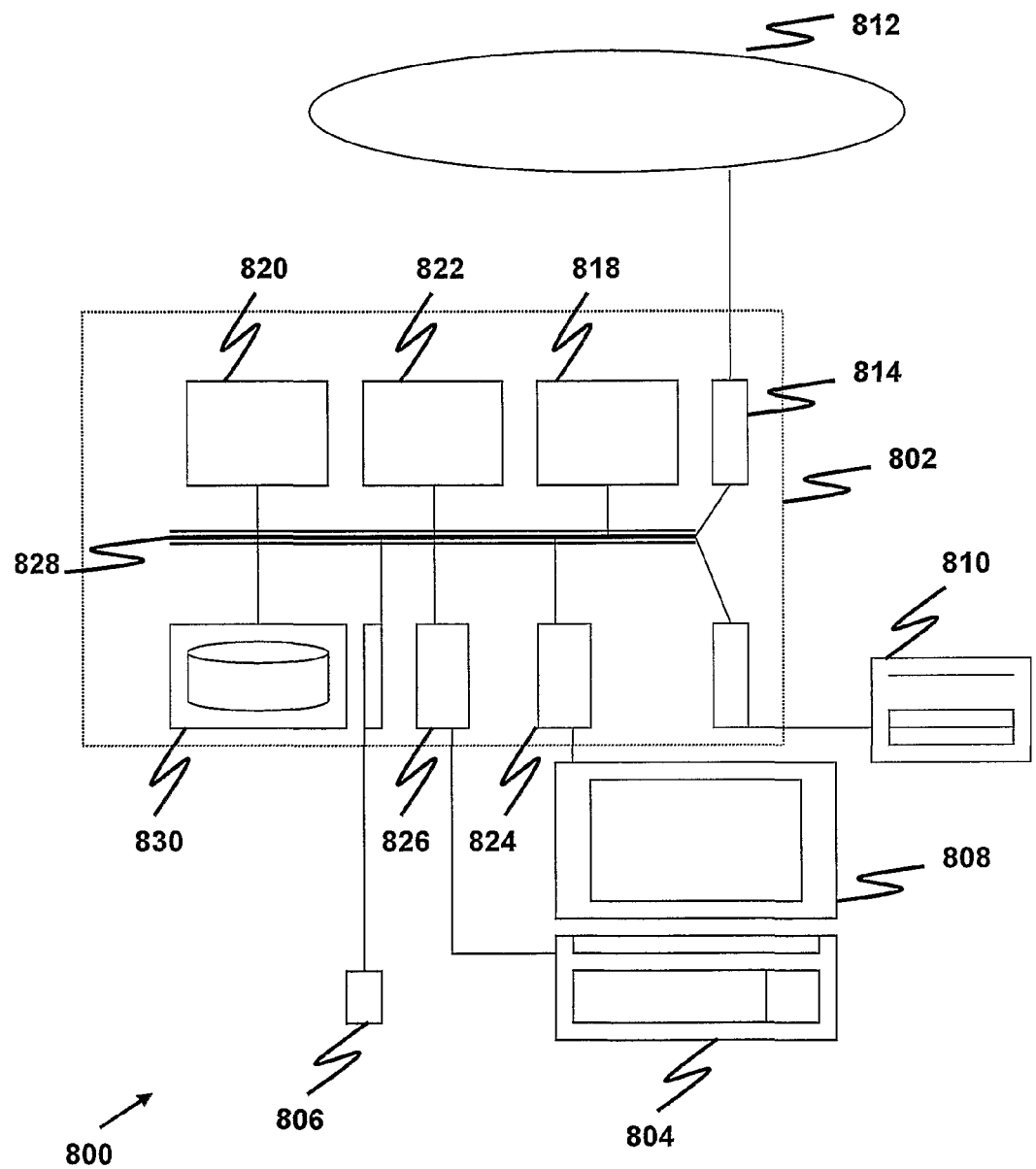
FIG. 8 shows a schematic diagram illustrating a computer system for implementing the method and system of the example embodiment.

The method and system of the example embodiment can be implemented on a computer system 800, schematically shown in FIG. 8. It may be implemented as software, such as a computer program being executed within the computer system 800, and instructing the computer system 800 to conduct the method of the example embodiment.

The computer system 800 comprises a computer module 802, input modules such as a keyboard 804 and mouse 806 and a plurality of output devices such as a display 808, and printer 810.

The computer module 802 is connected to a computer network 812 via a suitable transceiver device 814, to enable access to e.g. the Internet or other network systems such as Local Area Network (LAN) or Wide Area Network (WAN).

The computer module 802 in the example includes a processor 818, a Random Access Memory (RAM) 820 and a Read Only Memory (ROM) 822. The computer module 802 also includes a number of Input/Output (I/O) interfaces, for example I/O interface 824 to the display 808, and I/O interface 826 to the keyboard 804.

The components of the computer module 802 typically communicate via an interconnected bus 828 and in a manner known to the person skilled in the relevant art.

The application program is typically supplied to the user of the computer system 800 encoded on a data storage medium such as a CD-ROM or flash memory carrier and read utilising a corresponding data storage medium drive of a data storage device 830. The application program is read and controlled in its execution by the processor 818. Intermediate storage of program data maybe accomplished using RAM 820.

Although the present invention has been mainly described with respect to ADHD treatment, it can also find application for other mental disorders, such as depression, degraded working memory, Mild Cognitive Disorder (MCI), Alzheimer Disease (AD), etc. In addition, while the implementation of the present invention has been described as a system, it can also take the form of a software program with CDROM/DVD on a computer, a web-service over the internet, or a cartridge for a console, etc.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A device for generating a representation of a subject's attention level comprising:
   means for measuring brain signals from the subject;
   means for extracting temporal features from the brain signals;
   means for classifying the extracted temporal features using a classifier to give a score $x_1$;
   means for extracting spectral-spatial features from the brain signals;
   means for selecting spectral-spatial features containing discriminative information between concentration and non-concentration states from the set of extracted spectral-spatial features;
   means for classifying the selected spectral-spatial features using a classifier to give a score $x_2$;
   means for combining the scores $x_1$ and $x_2$ to give a single score; and
   means for presenting said single score to the subject.

2. The device as claimed in claim 1, wherein the means for presenting presents said single score in the form of a game.

3. The device as claimed in claim 2, wherein the means for presenting said single score adaptively adjusts at least one control parameter of the game based on said single score.

4. The device as claimed in claim 3, wherein the adjusting of said one control parameter comprises:
   presenting said game using a relationship between said single score and said one control parameter over a first period of time;
   determining a representative value for said single score of the subject over the first period of time;
   adjusting the relationship based on said representative value; and
   presenting said game using the adjusted relationship between said single score and said one control parameter over a second period of time.

5. The device as claimed in claim 4, wherein the adjusting of the relationship is such that a level of difficulty of the game in the second period of time is proportional to the representative value over the first period of time.

6. The device as claimed in claim 1, wherein the extracting of the temporal features from the brain signals comprises:
   computing statistics of brain waveforms in each of a plurality of electrode channels; and
   concatenating the statistics into a joint feature vector.

7. The device as claimed in claim 6, wherein the statistics of the brain waveforms are standard deviations.

8. The device as claimed in claim 1, wherein the extracting of the spectral-spatial features of the brain signals comprises:
   extracting respective brain signal components in discrete frequency windows using filter banks to obtain spectral features of brain signals; and
   applying a common spatial pattern (CSP) algorithm to each of the spectral features using a CSP array to obtain the spectral-spatial features of brain signals.

9. The device as claimed in claim 1, wherein the selecting of the spectral-spatial features containing discriminative information between concentration and non-concentration states from the set of extracted spectral-spatial features comprises selecting spectral-spatial features based on a mutual dependence of the extracted spectral-spatial features with respect to the concentration and non-concentration states.

10. The device as claimed in claim 1, wherein the combining of the scores $x_1$ and $x_2$ to give a single score comprises:
    normalizing the scores $x_1$ and $x_2$ according to an equation $(x-m_x)/s_x$, wherein $m_x$ and $s_x$ are the mean and standard deviation of outputs from the classifiers using training samples to give $x_{1n}$ and $x_{2n}$ respectively;
    assigning weights $w_1$ and $w_2$ to normalized scores $x_{1n}$ and $x_{2n}$ respectively; and
    combining the normalized scores $x_{1n}$ and $x_{2n}$ according to an equation $x_{1n}*w_1+x_{2n}*w_2$ to give the single score.

11. The device as claimed in claim 10, wherein said weights $w_1$ and $w_2$ are calculated according to the equation $w_i=(y_i)^p$ where $y_i$ is a classification accuracy in classifying the extracted temporal features if i=1 and in classifying the extracted spectral-spatial features if i=2 and p (p>0) controls the power of $w_i$ in the combination of the normalized scores $x_{1n}$ and $x_{2n}$ to give the single score.

12. The device as claimed in claim 1, wherein said classifier used to classify the extracted temporal features comprises one or more of a group consisting of a Linear Discriminant Analysis classifier, Neural Networks, Support Vector Machines, Fuzzy Inference System, Tree-based classifiers, Fuzzy Type 2 and Relevance Vector Machine.

13. The device as claimed in claim 1, wherein the device comprises a temporal feature extraction module, the temporal feature extraction module using training data to generate parameters for classifying the extracted temporal features using a classifier, for extracting spectral-spatial features from brain signals, for selecting spectral-spatial features containing discriminative information between the concentration and non-concentration states from the set of extracted spectral-spatial features and for classifying the selected spectral-spatial features using a classifier.

14. The device as claimed in claim 13, wherein said parameters comprise one or more of a group consisting of projection matrices of CSPs for the CSP algorithm, parameters for selecting spectral-spatial features based on mutual information and a model for the classifiers.

15. The device as claimed in claim 13, wherein the use of training data to generate parameters comprises:
   collecting training data from subjects performing a set of tasks; and
   determining said parameters via machine learning methods.

16. A method for generating a representation of a subject's attention level, the method comprising the steps of:
   using a computing system:
   measuring brain signals from the subject;
   extracting temporal features from the brain signals;
   classifying the extracted temporal features using a classifier to give a score $x_1$;
   extracting spectral-spatial features from the brain signals;
   selecting spectral-spatial features containing discriminative information between concentration and non-concentration states from the set of extracted spectral-spatial features;
   classifying the selected spectral-spatial features using a classifier to give a score $x_2$;
   combining the scores $x_1$ and $x_2$ to give a single score; and
   presenting said single score to the subject.

17. The method as claimed in claim 16, wherein presenting said single score to the subject comprises presenting said single score in the form of a game.

18. The method as claimed in claim 17, wherein presenting said single score to the subject comprises adaptively adjusting at least one control parameter of the game based on said single score.

19. The method as claimed in claim 18, wherein the adjusting of said one control parameter comprises:
   presenting said game using a relationship between said single score and said one control parameter over a first period of time;
   determining a representative value for said single score of the subject over the first period of time;
   adjusting the relationship based on said representative value; and
   presenting said game using the adjusted relationship between said single score and said one control parameter over a second period of time.

20. The method as claimed in claim 19, wherein the adjusting of the relationship is such that a level of difficulty of the game in the second period of time is proportional to the representative value over the first period of time.

21. The method as claimed in claim 16, wherein the extracting of the temporal features from the brain signals comprises:
   computing statistics of brain waveforms in each of a plurality of electrode channels; and
   concatenating the statistics into a joint feature vector.

22. The method as claimed in claim 21, wherein the statistics of the brain waveforms are standard deviations.

23. The method as claimed in claim 16, wherein the extracting of the spectral-spatial features of the brain signals comprises:
   extracting respective brain signal components in discrete frequency windows using filter banks to obtain spectral features of brain signals; and
   applying a common spatial pattern (CSP) algorithm to each of the spectral features using a CSP array to obtain the spectral-spatial features of brain signals.

24. The method as claimed in claim 16, wherein the selecting of the spectral-spatial features containing discriminative information between concentration and non-concentration states from the set of extracted spectral-spatial features comprises selecting spectral-spatial features based on a mutual dependence of the extracted spectral-spatial features with respect to the concentration and non-concentration states.

25. The method as claimed in claim 16, wherein the combining of the scores $x_1$ and $x_2$ to give a single score comprises:
   normalizing the scores $x_1$ and $x_2$ according to an equation $(x-m_x)/s_x$, wherein $m_x$ and $s_x$ are the mean and standard deviation of outputs from the classifiers using training samples to give $x_{1n}$ and $x_{2n}$ respectively;
   assigning weights $w_1$ and $w_2$ to normalized scores $x_{1n}$ and $x_{2n}$ respectively; and
   combining the normalized scores $x_{1n}$ and $x_{2n}$ according to an equation $x_{1n}*w_1+x_{2n}*w_2$ to give a single score.

26. The method as claimed in claim 25, wherein said weights $w_1$ and $w_2$ are calculated according to the equation $w_i=(y_i)^P$ where $y_i$ is a classification accuracy in classifying the extracted temporal features if i=1 and in classifying the extracted spectral-spatial features if i=2 and p (p>0) controls the power of $w_i$ in the combination of the normalized scores $x_{1n}$ and $x_{2n}$ to give the single score.

27. The method as claimed in claim 16, wherein said classifier used to classify the extracted temporal features comprises one or more of a group consisting of a Linear Discriminant Analysis classifier, Neural Networks, Support Vector Machines, Fuzzy Inference System, Tree-based classifiers, Fuzzy Type 2 and Relevance Vector Machine.

28. The method as claimed in claim 16, the method further comprises using training data to generate parameters for classifying the extracted temporal features using a classifier, for extracting spectral-spatial features from brain signals, for selecting spectral-spatial features containing discriminative information between the concentration and non-concentration states from the set of extracted spectral-spatial features and for classifying the selected spectral-spatial features using a classifier.

29. The method as claimed in claim 28, wherein said parameters comprise one or more of a group consisting of projection matrices of CSPs for the CSP algorithm, parameters for selecting spectral-spatial features based on mutual information and a model for the classifiers.

30. The method as claimed in claim 28, wherein using training data to generate parameters comprises:
   collecting training data from subjects performing a set of tasks; and
   determining said parameters via machine learning methods.

31. A non-transitory computer storage medium having stored thereon computer code means for instructing a computing device to execute a method of generating a representation of a subject's attention level, the method comprising the steps of:
   measuring brain signals from the subject;

extracting temporal features from the brain signals;
classifying the extracted temporal features using a classifier to give a score $x_1$;
extracting spectral-spatial features from the brain signals;
selecting spectral-spatial features containing discriminative information between concentration and non-concentration states from the set of extracted spectral-spatial features;
classifying the selected spectral-spatial features using a classifier to give a score $x_2$;
combining the scores $x_1$ and $x_2$ to give a single score; and
presenting said single score to the subject.

* * * * *